United States Patent [19]

Jakobson et al.

[11] Patent Number: 5,243,086
[45] Date of Patent: Sep. 7, 1993

[54] PROCESS FOR THE PREPARATION OF DIGLYCEROL AND/OR POLYGLYCEROL

[75] Inventors: Gerald Jakobson; Werner Siemanowski; Helmut Dillenburg, all of Rheinberg, Fed. Rep. of Germany

[73] Assignee: Deutsche Solvay-Werke, Solingen, Fed. Rep. of Germany

[21] Appl. No.: 951,008

[22] Filed: Sep. 25, 1992

[30] Foreign Application Priority Data

Sep. 27, 1991 [DE] Fed. Rep. of Germany ....... 4132171

[51] Int. Cl.$^5$ .............................................. C07C 41/01
[52] U.S. Cl. ..................................... 568/619; 568/680; 568/386
[58] Field of Search ..................... 568/619, 680, 386

[56] References Cited

U.S. PATENT DOCUMENTS 4,992,594 2/1991 Jakobson et al. ................. 568/680

FOREIGN PATENT DOCUMENTS 3900059 7/1990 Fed. Rep. of Germany .

Primary Examiner—Howard T. Mars
Attorney, Agent, or Firm—Foley & Lardner

[57] ABSTRACT

A process for the preparation of a composition containing diglycerol, in which process at least a stoichiometric amount of isopropylideneglycerol is reacted with α-monochlorohydrin in the presence of at least one alkaline compound at sufficient temperatures to yield an intermediate product composition containing monoisopropylidenediglycerol and a salt. Most of the salt and water formed is removed from the intermediate product composition, and any unreacted isopropylideneglycerol is removed by distillation. The remaining intermediate product composition containing monoisopropylidenediglycerol is subsequently reacted with water in the presence of at least one acidic catalyst at sufficient temperatures to yield a product composition containing diglycerol and acetone and substantially no cyclic glycerols.

19 Claims, No Drawings

PROCESS FOR THE PREPARATION OF DIGLYCEROL AND/OR POLYGLYCEROL

BACKGROUND OF THE INVENTION

The invention relates to the field of glycerols. In particular, the invention relates to a method for the preparation of a composition comprising diglycerol, and optionally, polyglycerols. The composition does not comprise undesirable cyclic glycerol compounds.

German Patent DE-OS 3,900,059 discloses a process for the preparation of polyglycerol, in which process α-monochlorohydrin is reacted with epichlorohydrin at temperatures of from 20° to 120° C. The molar ratio of epichlorohydrin to α-monochlorohydrin is from 0.8:1 to 1:2.5. They are reacted in the presence of acids or compounds which have an acidic reaction. The reaction mixture then is reacted with a medium in an alkaline reaction. Water is then added, and the product is demineralized by one or more cation exchangers and subsequent anion exchangers, and is separated by distillation into diglycerol and, if appropriate polyglycerol.

The shortcoming of this process is that the amounts of triglycerol, tetraglycerol and higher polyglycerols as well as the amount of cyclic components are relatively high when α-monochlorohydrin is reacted with epichlorohydrin. Moreover, a chlorine-containing compound which contaminates the polyglycerol is formed as a secondary product which can only be hydrolyzed with difficulty.

SUMMARY OF THE INVENTION

It is an aim and object of the present invention to utilize an improved process for the preparation of diglycerol. It also is an object of the present invention to utilize an improved process for the preparation of diglycerol either alone, or in combination with other polyglycerols such as triglycerol and tetraglycerol.

Other objects of the present invention include reducing the amount of cyclic components produced, obtaining diglycerol as the main product and substantially avoiding the formation of chlorine-containing organic compounds which are difficult to hydrolyze.

These and other objects apparent to those skilled in the art can be readily achieved by a process for the preparation of diglycerol comprising substantially no cyclic glycerol compounds. The product diglycerol also may include other polyglycerols such as triglycerol and tetraglycerol. In this process, isopropylideneglycerol is reacted with α-monochlorohydrin in the presence of at least one alkaline compound at reaction temperatures sufficient to yield monoisopropylidenediglycerol. Monoisopropylidenetriglycerol, monoisopropylidenetetraglycerol and other monoisopropylidenepolyglycerols also may be present if the reaction conditions favor the production of such products. The reaction mixture containing monoisopropylidenediglycerol and other products if present, is subsequently reacted with water in the presence of at least one acidic catalyst and possibly one acid ion exchanger at reaction temperatures sufficient to yield diglycerol, (triglycerol and other polyglycerols if reaction conditions favor the production of these compounds) and acetone.

DETAILED DESCRIPTION OF THE PREFERRED EMBODIMENTS

Throughout the specification and claims, the phrase "minor amount" and "substantially no" are treated synonymously, and are meant to include less than about 2% by weight. Preferably, substantially no cyclic components means less than about 1% by weight cyclic components are formed, and more preferably, less than about 0.5% by weight.

In accordance with the method of the invention, isopropylideneglycerol is reacted with α-monochlorohydrin in the presence of at least one alkaline compound, preferably an alkali metal hydroxide solution, at reaction temperatures sufficient to yield an intermediate product composition comprising monoisopropylidenediglycerol. In particular, the reaction temperature may be within the range of from about 10° to about 110° C., and preferably, from about 40° to about 100° C. The intermediate product stream also may comprise an amount of monoisopropylidenetriglycerol and monoisopropylidenetetraglycerol, and also may contain other monoisopropylidenepolyglycerols if reaction conditions favor the production of these compounds. Such reaction conditions typically include those in which an excess (based on a stoichiometric reaction) of isopropylideneglycerol is employed. Persons of ordinary skill in the art recognize other reaction conditions which may yield these compounds.

A majority of the salt or salts and, if water is formed, the water formed, are separated from the intermediate product composition, and any excess isopropylideneglycerol is removed by distillation. The monoisopropylidenediglycerol, (and monoisopropylidenetriglycerol and other monoisopropylidenepolyglycerols if present) is subsequently reacted with water in the presence of at least one acidic catalyst or one acid ion exchanger. This reaction typically occurs at reaction temperatures sufficient to yield a product composition comprising diglycerol and acetone. Triglycerol, tetraglycerol and other polyglycerols also may be produced. Preferably, the reaction temperature of the second reaction is within the range of from about 20° to about 110° C., and more preferably within the range of from about 60° to about 100° C.

In a preferred embodiment of the invention, isopropylideneglycerol is reacted with α-monochlorohydrin in the presence of alkali metal hydroxide, preferably sodium hydroxide or sodium hydroxide solution, in a molar ratio of α-monochlorohydrin to alkali metal hydroxide, (calculated as solid substance), of from about 1:1.001 to about 1:1.5, and more preferably from about 1:1.005 to about 1:1.3. Maintaining the molar ratio of α-monochlorohydrin to NaOH within this range results in an accelerated reaction which is approximately quantitative.

When isopropylideneglycerol is reacted with α-monochlorohydrin, the isopropylideneglycerol and the alkaline compound, preferably an alkali metal hydroxide, first are introduced into the reaction vessel, and then α-monochlorohydrin is added. In a particularly preferred embodiment, α-monochlorohydrin is added continuously. If the reactants are not added in accordance with this sequence, there is a risk of the formation of other compounds, in particular, cyclic compounds.

In another preferred embodiment, isopropylideneglycerol is reacted with α-monochlorohydrin in a molar ratio of from about 1.001:1 to about 20:1, and more preferably from about 4:1 to about 10:1. By maintaining the molar ratio of components within this range, the amount of cyclic compounds produced can further be reduced. Furthermore, maintenance of a molar ratio within this range increases the ratio of diglycerol to polyglycerol ultimately produced by increasing the ratio of monoisopropylidenediglycerol to monoisopropylidenepolyglycerol present in the intermediate product composition.

In accordance with the present invention, when the reaction to monoisopropylidenediglycerol has taken place and the water in the intermediate product stream has been removed by distillation, the salt which has precipitated typically is separated off. In particular, the salt is separated by filtration or centrifugation. If the water component is distilled off during the reaction, then the salt which is formed is difficult to filter or separate. In a particularly preferred embodiment, the salt which has precipitated is sodium chloride.

Typically, upon removal of the salt, the isopropylideneglycerol which had been employed in excess is removed by distillation and recirculated to the reaction. Also, the product acetone, obtained during the aqueous hydrolysis of monoisopropylidenediglycerol under acidic catalysis, is circulated and used concomitantly for the preparation of isopropylideneglycerol from glycerol and acetone. Regenerating these components permits optimization of the process.

As a final separation, the di-, tri- and polyglycerols present in the product composition and formed after ketal cleavage in aqueous solution with acidic catalysis typically are freed from acetone by distillation and may comprise an amount of glycerol (formed from incompletely distilled isopropylideneglycerol during the hydrolysis). The product glycerols then are freed from the dissolved residual salt content, (preferably sodium chloride), by a combination of at least one cation exchanger followed by at least one anion exchanger and subsequently separated into water, glycerol, diglycerol and polyglycerols by fractional distillation. In a further embodiment, the polyglycerols may be separated into tri-, tetra- and/or higher polyglycerols by fractional distillation.

Skilled practitioners are familiar with the conditions necessary to carry out the separation of the salt via anion exchange and cation exchange as well as those conditions necessary to separate the products into their respective glycerols via fractional distillation. Other methods of separation known to those skilled in the art also may be utilized.

The foregoing description and the following examples represent preferred embodiments of the present invention and are in no way limiting thereof. Various modifications and variations may be made by those having ordinary skill in the art without departing from the spirit and scope of the invention described in the appended claims.

EXAMPLES

EXAMPLE 1

Two mol (264 g) isopropylideneglycerol and 1.1 mol of sodium hydroxide (in the form of a 50% aqueous solution) first were introduced into a 1-l double-wall reactor equipped with stirrer and distillation head, and heated to approx. 90° C. Then, approximately 1 mol (110.5 g) of α-monochlorohydrin was continuously metered into the reactor at this temperature over the course of 2 hours, with stirring. The reaction mixture then was allowed to after-react for half an hour, the water which was present distilled off in vacuo and the salt which was precipitated subsequently filtered off.

The filtrate was recycled to the reactor, and the isopropylideneglycerol, which had been employed in excess, was distilled off at a fuel oil temperature (oil bath temperature) of 120° C. and at 20 mbar.

The residue in the reactor was treated with the same volumetric amount of distilled water and acidified using concentrated HCl solution (30% by weight). The acetone produced was distilled off at a fuel oil temperature (oil bath temperature) of 100° C. (duration of the ketal cleavage was approximately 0.5 hours).

The aqueous crude diglycerol solution then was demineralized by a combination of a cation and an anion exchanger and subsequently evaporated in vacuo. Approximately 126 g were obtained as crude product. The crude product then was analyzed by gas chromatography, and the results are listed in Table I below.

TABLE I

| GC analysis of the crude product (g/kg) | |
| --- | --- |
| Glycerol | 160.2 |
| Cyclic diglycerol | 2.5 |
| Diglycerol | 608.6 |
| Cyclic triglycerol | 1.2 |
| Triglycerol | 162.3 |
| Cyclic tetraglycerol | 1.2 |
| Tetraglycerol | 46.3 |
| Cyclic pentaglycerol | 4.9 |
| Pentaglycerol | 8.4 |
| Hexaglycerol | 3.3 |
| Heptaglycerol | 1.0 |

EXAMPLE 2

The procedure of Example 1 was repeated except 6 mol (793 g) of isopropylideneglycerol and 1.03 mol (41 g) of sodium hydroxide (50% aqueous solution) were introduced to the reactor which was heated to 30° C. Then, as in Example 1 mol (110.5 g) of α-monochlorohydrin was continuously metered at this temperature over the course of 2 hours. Upon separation and additional reaction, as in Example 1, approximately 135 grams of crude product were obtained. The gas chromatography analysis rendered the results set forth in Table II below.

TABLE II

| GC analysis of the crude product (g/kg) | |
| --- | --- |
| Glycerol | 78.5 |
| Cyclic diglycerol | 18.7 |
| Diglycerol | 717.3 |
| Cyclic triglycerol | 6.2 |
| Triglycerol | 133.8 |
| Cyclic tetraglycerol | 1.7 |
| Tetraglycerol | 31.7 |
| Cyclic pentaglycerol | 1.0 |
| Pentaglycerol | 8.3 |
| Hexaglycerol | 2.3 |

EXAMPLE 3

The procedure of Examples 1 and 2 as repeated except that 8 mol (1056 g) of isopropylideneglycerol and 1.1 mol (44 g) of sodium hydroxide (50% aqueous solution) were introduced to the reactor which was heated to 90° C. Then, as in Example 1 mol (110.5 g) of α-monochlorohydrin was continuously metered at this temperature over the course of 2 hours. Upon separation and additional reaction as in Example 1, approximately 147 grams of crude product were obtained. The gas chromatography analysis rendered the results set forth in Table III below.

TABLE III

| GC analysis of the crude product (g/kg) | |
| --- | --- |
| Glycerol | 75.0 |
| Cyclic diglycerol | 1.2 |
| Diglycerol | 815.8 |
| Cyclic triglycerol | 1.2 |
| Triglycerol | 90.4 |
| Tetraglycerol | 13.6 |
| Pentaglycerol | 1.7 |

The crude products of Examples 1 to 3 Were subjected to fractional distillation and separated into glycerol, diglycerol and polyglycerol.

As can be seen from the above Tables I–III, substantially no cyclic glycerol components, as well as no chlorine-containing organic compounds were produced when the method of the present invention was carried out.

What is claimed is:

1. A process for the preparation of a composition comprising diglycerol and substantially no cyclic glycerols, said process comprising the steps of:
   (a) reacting at least a stoichiometric amount of isopropylideneglycerol and α-monochlorohydrin in the presence of an alkaline material at a first reaction temperature sufficient to yield an aqueous intermediate product composition comprising monoisopropylidenediglycerol and a salt;
   (b) separating said salt and water from said intermediate product composition, and separating excess unreacted isopropylideneglycerol by distillation;
   (c) reacting the remaining intermediate product composition with water in the presence of at least one acidic catalyst at a second reaction temperature sufficient to yield an aqueous product composition comprising diglycerol and acetone, and substantially no cyclic glycerols; and
   (d) separating said acetone from said product composition.

2. A process as claimed in claim 1, wherein said first reaction temperature is within the range of from about 10° to about 110° C.

3. A process as claimed in claim 2, wherein said first reaction temperature is within the range of from about 40° to about 100° C.

4. A process as claimed in claim 1, wherein said second reaction temperature is within the range of from about 20° to about 110° C.

5. A process as claimed in claim 4, wherein said second reaction temperature is within the range of from about 60° to about 100° C.

6. A process as claimed in claim 1, wherein said intermediate product composition further comprises monoisopropylidenetriglycerol and monoisopropylidenetetraglycerol.

7. A process as claimed in claim 6, wherein said product composition further comprises triglycerol and tetraglycerol.

8. A process as claimed in claim 1, wherein isopropylideneglycerol is reacted with α-monochlorohydrin in step (a) at a molar ratio within the range of from about 1.001:1 to about 20:1.

9. A process as claimed in claim 8, wherein isopropylideneglycerol is reacted with α-monochlorohydrin in step (a) at a molar ratio within the range of from about 4:1 to about 10:1.

10. A process as claimed in claim 1, wherein said alkaline material comprises an alkali metal hydroxide solution.

11. A process as claimed in claim 10, wherein α-monochlorohydrin is reacted in step (a) at a α-monochlorohydrin to alkali metal hydroxide molar ratio within the range of from about 1:1.001 to about 1:1.5.

12. A process as claimed in claim 11, wherein α-monochlorohydrin is reacted in step (a) at a α-monochlorohydrin to alkali metal hydroxide molar ratio within the range of from about 1:1.005 to about 1:1.3.

13. A process as claimed in claim 1, wherein α-monochlorohydrin in step (a) is added continuously to the reaction mixture of isopropylideneglycerol and alkaline material.

14. A process as claimed in claim 1, wherein the separation of said salt in step (b) is by filtration or centrifugation.

15. A process as claimed in claim 1, further comprising the step of recirculating said acetone separated in step (d) to produce isopropylideneglycerol by reaction with glycerol.

16. A process as claimed in claim 1, further comprising the step of:
   subjecting the product composition to at least one cation exchange followed by at least one anion exchange to remove dissolved residual salt.

17. A process as claimed in claim 7, further comprising the steps of:
   (e) subjecting the product composition to at least one cation exchange followed by at least one anion exchange to remove dissolved residual salt; and
   (f) subjecting the resulting product composition from step (e) to fractional distillation to separate said product composition into water, glycerol, diglycerol, triglycerol and tetraglycerol.

18. A process as claimed in claim 1, further comprising the step of recirculating said isopropylideneglycerol separated in step (b) to step (a).

19. A process as claimed in claim 1, wherein the process is carried out as a continuous process.

* * * * *